United States Patent
Huang et al.

(10) Patent No.: US 11,771,787 B2
(45) Date of Patent: Oct. 3, 2023

(54) DISINFECTION SYSTEM AND ELEVATOR EQUIPMENT HAVING THE SAME

(71) Applicant: GRAND MATE CO., LTD., Taichung (TW)

(72) Inventors: Chung-Chin Huang, Taichung (TW); Chin-Ying Huang, Taichung (TW); Hsin-Ming Huang, Taichung (TW); Hsing-Hsiung Huang, Taichung (TW); Yen-Jen Yeh, Taichung (TW); Soong-Jack Chow, Lexington, KY (US); Soong-Wai Chow, Singapore (SG)

(73) Assignee: GRAND MATE CO., LTD., Taichung (TW)

( * ) Notice: Subject to any disclaimer, the term of this patent is extended or adjusted under 35 U.S.C. 154(b) by 329 days.

(21) Appl. No.: 17/170,225

(22) Filed: Feb. 8, 2021

(65) Prior Publication Data
US 2022/0016288 A1 Jan. 20, 2022

(30) Foreign Application Priority Data
Jul. 16, 2020 (TW) .................................. 109124001

(51) Int. Cl.
*A61L 2/24* (2006.01)
*A61L 2/10* (2006.01)
*B66B 1/34* (2006.01)

(52) U.S. Cl.
CPC .................. *A61L 2/24* (2013.01); *A61L 2/10* (2013.01); *B66B 1/3492* (2013.01); *A61L 2202/14* (2013.01); *A61L 2202/25* (2013.01)

(58) Field of Classification Search
CPC .......... A61L 2/10; A61L 2/24; A61L 2202/14; A61L 2202/25; B66B 1/3492
(Continued)

(56) References Cited

U.S. PATENT DOCUMENTS

| 2007/0023710 | A1* | 2/2007 | Tom | A61L 2/10 |
| | | | | 422/62 |
| 2013/0341533 | A1* | 12/2013 | Leben | A61L 2/10 |
| | | | | 250/492.1 |

FOREIGN PATENT DOCUMENTS

| CN | 102416187 A | 4/2012 |
| CN | 202554523 U | 11/2012 |

(Continued)

OTHER PUBLICATIONS

Search report for TW109124001, dated Dec. 18, 2020, Total of 1 page.
(Continued)

*Primary Examiner* — Nicole M Ippolito
(74) *Attorney, Agent, or Firm* — Apex Juris, pllc; Hilde Coeckx

(57) ABSTRACT

A disinfection system includes an ultraviolet disinfecting light, a controlling device, and an ultraviolet detecting device. The ultraviolet disinfecting light can be turned on or off under control. The controlling device controls the ultraviolet disinfecting light to be turned on or off. The ultraviolet detecting device is signally connected to the controlling device and is for detecting an intensity of the ultraviolet rays emitted by the ultraviolet disinfecting light. The controlling device controls the ultraviolet disinfecting light to increase an ultraviolet radiation dose of the ultraviolet rays emitted by the ultraviolet disinfecting light after the ultraviolet disinfecting light is turned on and the intensity of the ultraviolet rays is less than a predetermined intensity. An elevator equipment includes a car, a lift control device, and the disinfection system. In this way, the space can be disinfected with the ultraviolet rays to avoid insufficient disinfection effect.

18 Claims, 13 Drawing Sheets

(58) Field of Classification Search
USPC ............... 250/453.11, 454.11, 455.11, 504 R
See application file for complete search history.

(56) References Cited

FOREIGN PATENT DOCUMENTS

| | | |
|---|---|---|
| CN | 208419020 U | 1/2019 |
| CN | 110585455 A | 12/2019 |
| CN | 111202861 A | 5/2020 |
| JP | 2015000111 A | 1/2015 |
| TW | 584149 U | 4/2004 |
| WO | 2005062734 A2 | 7/2005 |

OTHER PUBLICATIONS

English abstract for CN202554523, Total of 1 page.
English abstract for CN208419020, Total of 1 page.
English abstract for TW584149, Total of 1 page.
Search report for SG application 10202006868S, dated May 20, 2021, Total of 3 pages.
English Abstract for JP2015000111, Total of 1 page.
English Abstract for CN102416187, Total of 1 page.
English Abstract for CN110585455, Total of 1 page.
English Abstract for CN111202861, Total of 1 page.

* cited by examiner

US 11,771,787 B2

DISINFECTION SYSTEM AND ELEVATOR EQUIPMENT HAVING THE SAME

TECHNICAL FIELD

The present invention is related to a disinfection system and an elevator equipment, and more particularly to a disinfection system with an ultraviolet disinfecting light and an elevator equipment thereof.

DESCRIPTION OF RELATED ART

With the development of society, various business activities, social events, and leisure activities get more and more active, and interpersonal communication is more frequent as well. However, it has led to several infectious pandemics in recent years, such as SARS, MERS, and COVID-19. The infection routes of viruses, bacteria, and other infection sources spread through physical contact or droplet, and the risk of infection is on the rise due to the inevitable close contact between people.

Take an elevator as an example, people come and go in there, and yet the space of the car thereof is narrow and small. During the lift, the car forms an enclosed space, resulting in a high-risk area where infection sources exist.

To avoid passengers being infected by infection sources, the cleaning staff of the existing elevators mostly wipe the interior of the car with disinfectant regularly. Even though the passengers who take the elevator reduce the risk of infection, wiping the interior of the car increases the labor cost and the risk of cleaning staff being infected. Moreover, elevator hours vary. Between two cleaning operations, maybe no one takes the elevator, which results in the waste of cleaning manpower.

There are some cars of elevators provided with ultraviolet disinfecting lights, where the interior of the cars can be disinfected by the ultraviolet light emitted by the ultraviolet disinfecting light so as to prevent the inconvenience of manpower cleaning. However, the intensity of ultraviolet rays emitted in the space varies due to the installation angle or the number of uses of the ultraviolet disinfecting light, and insufficient intensity of ultraviolet rays leads to poor disinfection effect. The user has difficulties to know whether the intensity of ultraviolet rays is sufficient or not.

BRIEF SUMMARY OF THE INVENTION

In view of the above, the object of the invention is to provide a disinfection system and an elevator equipment with the same that will increase an ultraviolet radiation dose of the ultraviolet rays when the intensity of ultraviolet is insufficient.

The present invention provides a disinfection system applied to a space. The space has an entrance communicating with an outside thereof. The disinfection system includes an ultraviolet disinfecting light, a controlling device, and an ultraviolet detecting device. The ultraviolet disinfecting light can be turned on or off under control and emits ultraviolet rays to the space when it is turned on. The controlling device is connected to the ultraviolet disinfecting light and controls the ultraviolet disinfecting light to be turned on or off. The ultraviolet detecting device is signally connected to the controlling device and is for detecting an intensity of the ultraviolet rays emitted by the ultraviolet disinfecting light. The controlling device controls the ultraviolet disinfecting light to increase an ultraviolet radiation dose of the ultraviolet rays emitted by the ultraviolet disinfecting light after the ultraviolet disinfecting light is turned on and the intensity of the ultraviolet rays is less than a predetermined intensity.

The present invention provides an elevator equipment including a car, a lift control device, and the disinfection system. The space located inside the car. The lift control device is for controlling the lift of the car. The disinfection system is installed at the car.

The advantage of the present invention is that when the intensity of ultraviolet rays is insufficient, the ultraviolet radiation dose will be increased to avoid insufficient disinfection effect.

The present invention further provides a disinfection system including an ultraviolet disinfecting light, a detecting device, and a controlling device. The ultraviolet disinfecting light can be turned on or off under control and emits ultraviolet rays to the space when it is turned on. The detecting device detects a temperature and a movement state in the space. The movement state is one of a first state and a second state, wherein the first state indicates that there is no moving target in the space and the second state indicates that a moving target is in the space. The controlling device is connected to the detecting device and the ultraviolet disinfecting light. The controlling device controls the ultraviolet disinfecting light to be turned on when the detecting device detects that the temperature is less than a predetermined temperature and the movement state is the first state.

In this way, taking the temperature and the movement state as a double-check, the space without a moving target is automatically disinfected by the ultraviolet rays. When there is a moving target (a human being or an animal) in the space, the disinfection system can effectively avoid the ultraviolet disinfecting light to be turned on by mistake, not causing damages to the moving target.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
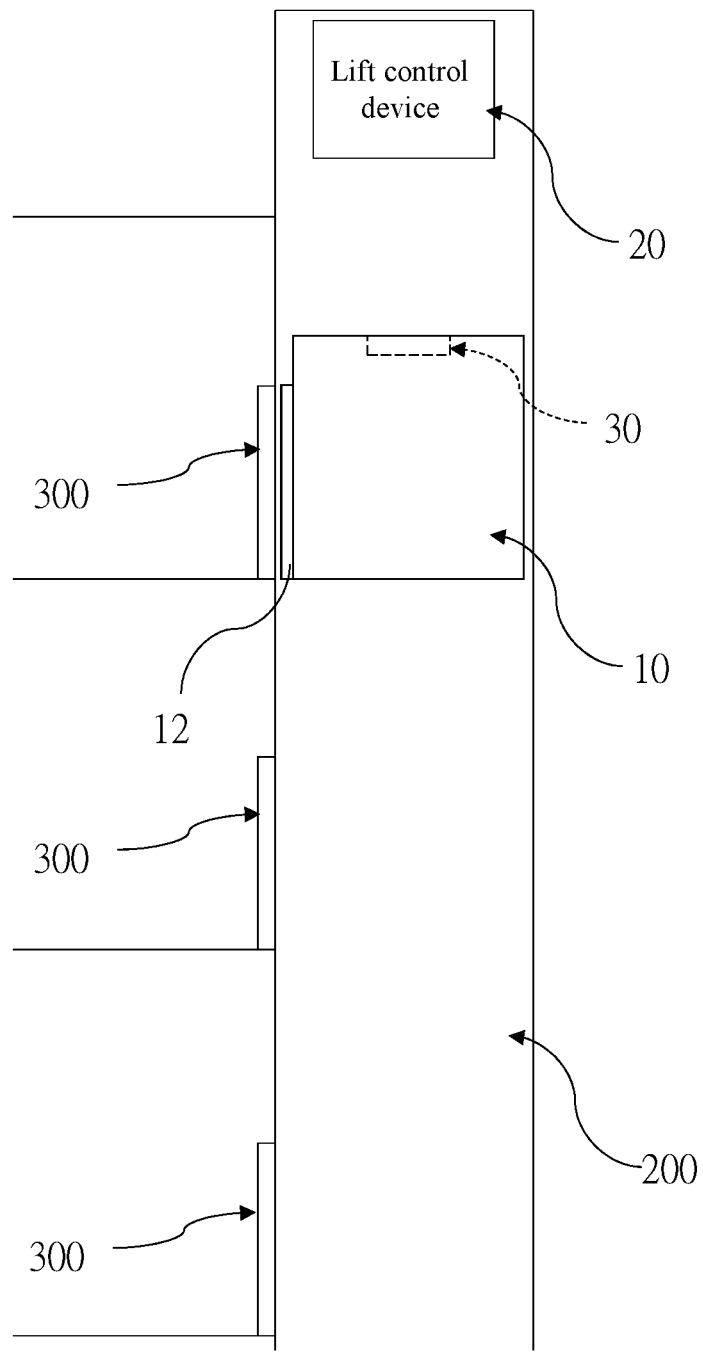
FIG. 1 is a schematic view of an elevator equipment of a first embodiment according to the present invention.
Figure 2:
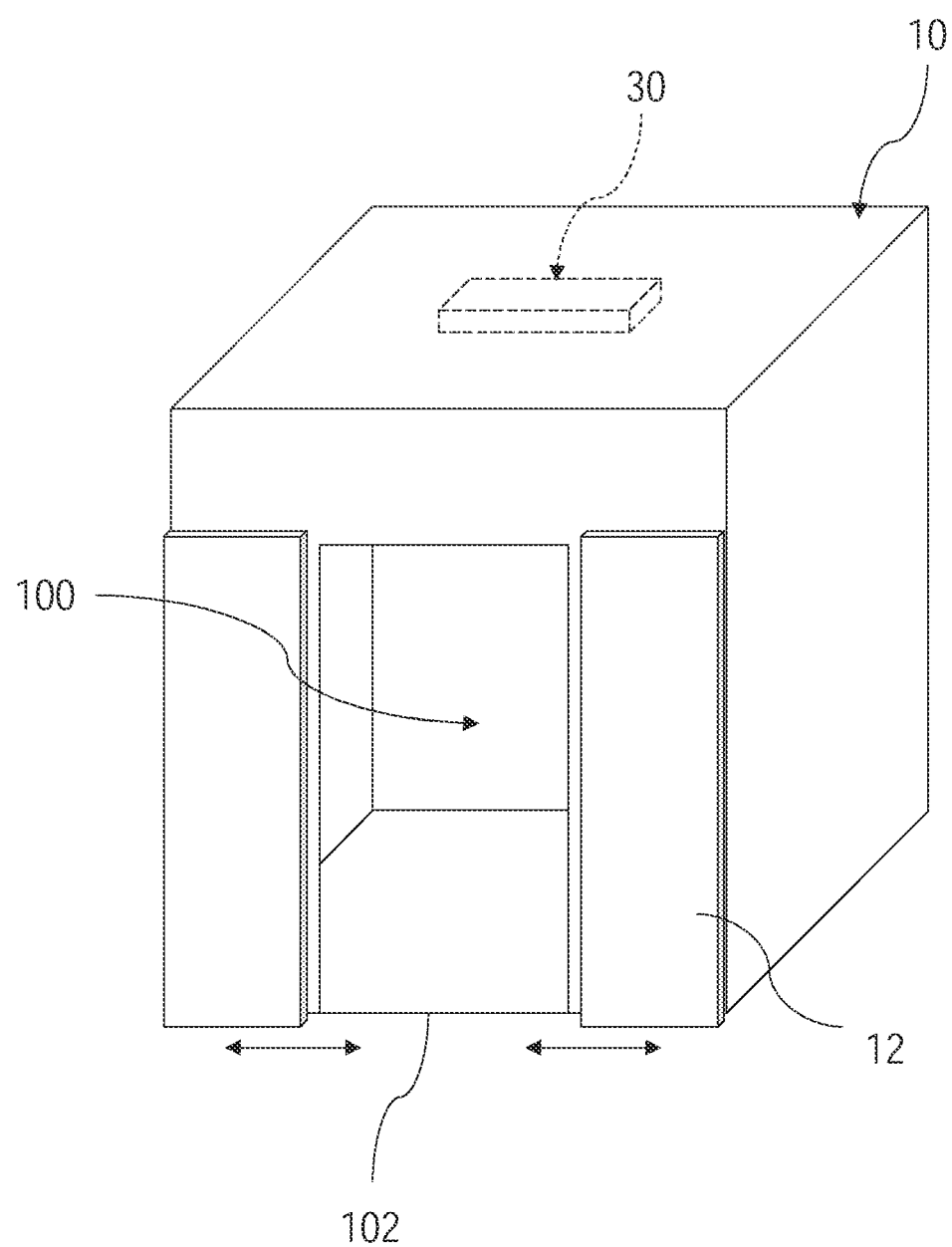
FIG. 2 is a schematic perspective view of a car of the elevator equipment of the first embodiment.
Figure 3:
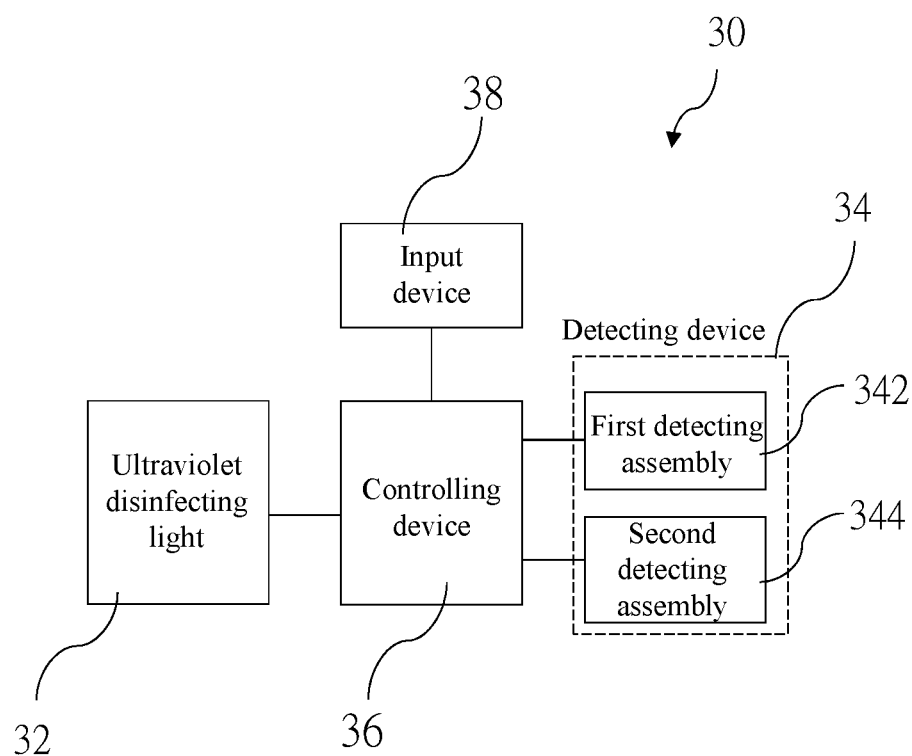
FIG. 3 is a block diagram of a disinfection system of the first embodiment.

The following illustrative embodiments and drawings are provided to illustrate the disclosure of the present invention, these and other advantages and effects can be clearly understood by persons skilled in the art after reading the disclosure of this specification. As illustrated in FIG. 1 and FIG. 2, an elevator equipment of a first embodiment according to the present invention includes a car 10, a lift control device 20, and a disinfection system 30.

The car 10 is movably installed in a hoistway 200 of a building. Inside the car 10 is a space 100 which has an entrance 102 communicating with an outside thereof. The car is provided with a door 12 located at the entrance 102 and movably blocking the entrance 102.

The lift control device 20 is for controlling the lift of the car 10 to move between different floors in the hoistway 200. For example, the car 10 can be driven by ropes (not shown). When the car 10 moves to a certain floor, the lift control device 20 controls the opening of an outer door 300 and the door 12 of the car 10 for passengers to get in and out of the space 100 of the car 10 through the entrance 102.

The disinfection system 30 is installed at the car 10 and connected to the lift control device 20. In the current embodiment, the disinfection system 30 is located at a top of the space of the car 10 and is used to disinfect the space 100, but it is not limited thereto, the disinfection system 30 can also be installed at an appropriate position. The disinfection system 30 includes an ultraviolet disinfecting light 32, a detecting device 34, and a controlling device 36, The ultraviolet disinfecting light 32 can be turned on or off under control and emits ultraviolet rays to the space 100 when it is turned on. The ultraviolet disinfecting light 32 includes a plurality of ultraviolet light emitting components for emitting ultraviolet rays, which are a plurality of ultraviolet light emitting diodes (UV LED) as an example in the current embodiment. In one embodiment, the ultraviolet disinfecting light 32 can also adopt ultraviolet light emitting components, such as at least one ultraviolet light emitting diode or at least one ultraviolet lamp tube, to emit ultraviolet rays.

The detecting device 34 detects a temperature and a movement state in the space. In the current embodiment, the detecting device 34 includes a first detecting assembly 342 and a second detecting assembly 344. The first detecting assembly 342, which may be a pyroelectric infrared radial sensor (PIR Sensor) as an example, is for detecting the temperature and the movement state. When there is no heat-generating target (such as a human being or an animal) in the space, the temperature detected by the first detecting assembly 342 is the background temperature of the space and the detected movement is a first state, that is, there is no moving target in the space. When a heat-generating target enters the space 100, the temperature detected by the first detecting assembly 342 is the temperature of the moving target and the detected movement state is a second state, that is, there is a moving target in the space 100. In one embodiment, the first detecting assembly 342 can also adopt a thermal imaging sensor.

The second detecting assembly 344 is for detecting detecting whether the door 12 blocks the entrance or not. The second detecting assembly 344 may be, for example, an ultrasonic sensor, which emits ultrasonic waves from the top of the space 100 to the entrance 102 to detect whether the door 12 blocks the entrance 102 or not.

The controlling device 36 is electrically connected to the detecting device 34 and the ultraviolet disinfecting light 32, but it is not limited thereto, the controlling device 36 can also be connected wirelessly to the detecting device.

When the detecting device 34 detects that the door 12 blocks the entrance 102, the controlling device 36 performs the following control steps:

When the detecting device 34 detects that the temperature is less than a predetermined temperature and the movement state is the first state, the controlling device 36 controls the ultraviolet disinfecting light 32 to be turned on. In the current embodiment, the predetermined temperature ranges between 30° C. and 33° C. In other words, if the controlling device 35 determines that there is no heat-generating moving target in the space of the car 10 at present, the space 100 of the car 10 is going to be disinfected.

If the temperature is higher than the predetermined temperature or the movement state is the second state, which means that there is still a human being or an animal in the space 100, the ultraviolet disinfecting light 32 is controlled not to be turned on.

In this way, when there is a moving target (a human being or animal) in the space 100, taking the temperature and the movement state as a double-check can effectively avoid the ultraviolet disinfecting light to be turned on by mistake, not causing damages to the moving target.

In the current embodiment, after the controlling device 36 controls the ultraviolet disinfecting light 32 to be turned on, the ultraviolet disinfecting light 32 is controlled to be turned off if any one of the following closing conditions is met. The closing conditions include:

1. The door 12 does not block the entrance; namely, the door 12 is open. When the detecting device 34 detects that the door 12 does not block the entrance 102, the controlling device 36 controls the ultraviolet disinfecting light 32 to be turned off.

2. There is a moving target in the space 100. When the detecting device 34 detects that the temperature of the space 100 is higher than the predetermined temperature or the movement state is the second state, the controlling device 36 controls the ultraviolet disinfecting light 32 to be turned off. For example, when the door 12 blocks the entrance and a moving target in the space 100 is covered by an obstacle that has a temperature less than the predetermined temperature, the moving target cannot be detected. After moving the obstacle, the moving target is detected and the ultraviolet disinfecting light 32 is turned off accordingly.

3. The controlling device 36 controls the ultraviolet disinfecting light 32 to be turned on and after an irradiation time, the ultraviolet disinfecting light 32 is controlled to be turned off. The controlling device 36 starts timing after the ultraviolet disinfecting light 32 is controlled to be turned on. When the time counted reaches the irradiation time, the ultraviolet disinfecting light 32 is controlled to be turned off. In the current embodiment, the disinfection system 30 may optionally include an input device 38 which is connected to the controlling device 36 in a wired or wireless manner and has buttons or a touch screen for a user to operate and to input a time value. The controlling device 36 sets the irradiation time with the time value to change the disinfection time. In addition, when the user confirms there is no moving target in the space 100, the user can operate the input device 38 to output an activation signal to the controlling device 36, and the controlling device 36 accordingly controls the ultraviolet disinfecting light 32 to be turned on.

After the ultraviolet disinfecting light 32 is turned off, the detecting device 34 continues to detect whether the door 12 is open or not. When the detecting device 34 detects that the door 12 continues to block the entrance 102, the controlling device 36 keeps the ultraviolet disinfecting light 32 off. Namely, if no one or an animal enters the space 100 after disinfection, the controlling device 36 no longer disinfects the space 100 until it detects that a person or an animal enters the space 100 and leaves, then the ultraviolet disinfecting device 32 will be turned on again to disinfect the space 100.

Figure 4:
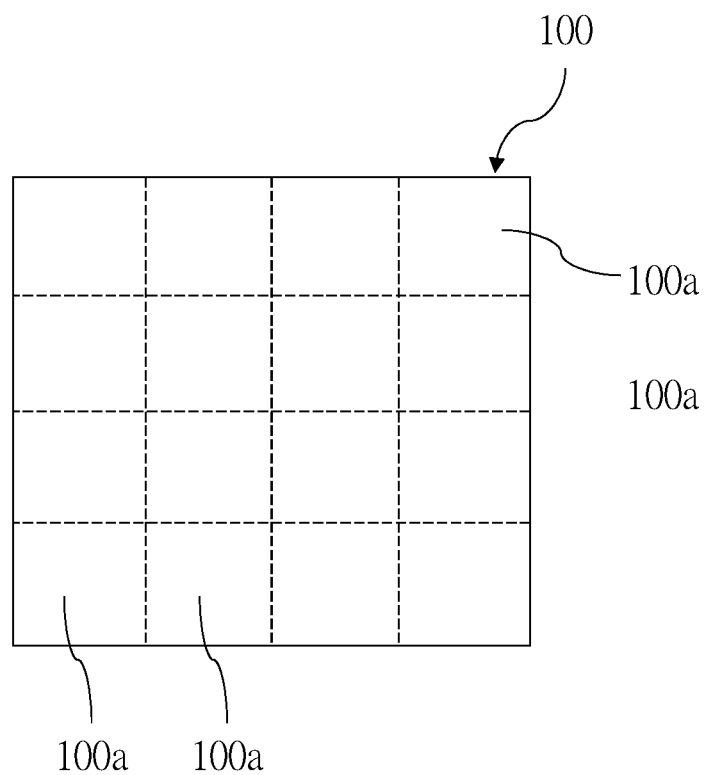
FIG. 4 is a block diagram of a disinfection system of a second embodiment according to the present invention.

As shown in FIG. 4, the detecting device 34 of the elevator equipment of a second embodiment according to the present invention divides the space into a plurality of detection areas 100a and detects the temperature and the movement states of each detection area 100a. When the temperature detected at any detection area 100a appears a predetermined temperature difference within a predetermined time, the temperature detected at any detection area 100a is higher than the predetermined temperature, or the movement state detected at any detection area 100a is the second state, the controlling device 36 records the corresponding detection area as an enhanced area. For example, the user can set the predetermined time between 5 and 10 minutes and set the predetermined temperature difference of ±5 to 20° C. It indicates that a moving target enters or moves out of the corresponding detection area if there is a temperature difference of ±5 to 20° C. within 5 to 10 minutes. After that, the controlling device 36 controls the ultraviolet disinfecting light 32 to be turned on and to increase the ultraviolet radiation dose of the enhanced area when the detecting device 34 detects that the temperature of each detection area 100a is less than the predetermined temperature and the movement state is the first state.

Figure 5:
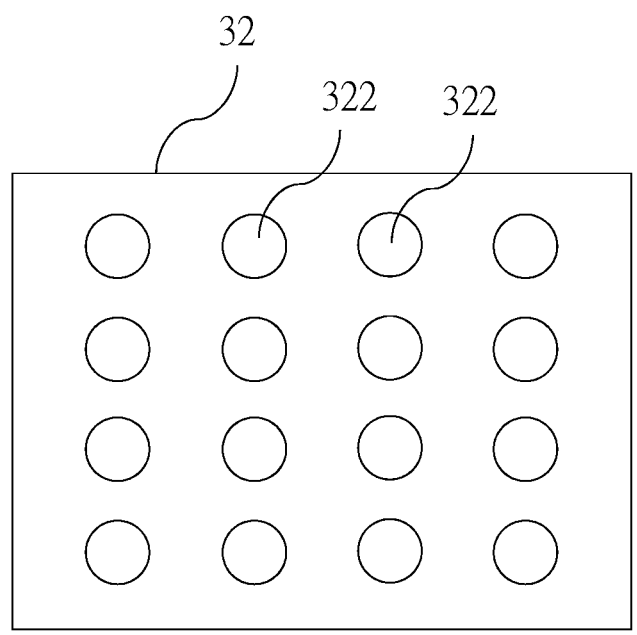
FIG. 5 is a schematic view of ultraviolet disinfecting lights of the disinfection system of the second embodiment.

Taking the ultraviolet disinfecting light 32 in FIG. 5 as an example, it includes a plurality of ultraviolet light emitting diodes 322. The ultraviolet light emitting diodes 322 respectively correspond to the detection areas 100a, and the controlling device 36 individually controls the ultraviolet light emitting diodes 322 to be turned on or off. Ways to increase the ultraviolet radiation dose include the followings:

1. During an irradiation time, the controlling device 36 controls the intensity of the ultraviolet rays of the ultraviolet light emitting diode 322 corresponding to the enhanced area to be a first light intensity and controls the intensity of the ultraviolet rays of the ultraviolet light emitting diode 322 corresponding to the other detection area to be a second light intensity. The first light intensity is greater than the second light intensity.

2. During a first irradiation time, the controlling device 36 controls the intensity of the ultraviolet light emitting diodes 322 to be the same light intensity. After reaching the first irradiation time, the controlling device 36 keeps the ultraviolet light emitting diode 322 corresponding to the enhanced area to be turned on and controls the ultraviolet light emitting diode 322 corresponding to the other detection area to be turned off. After reaching a second irradiation time, the controlling device 36 controls the ultraviolet light emitting diode 322 corresponding to the enhanced area to be turned off.

Thereby, the disinfection effect of the detection areas 100a where a person or an animal has once appeared can be enhanced.

Figure 6:
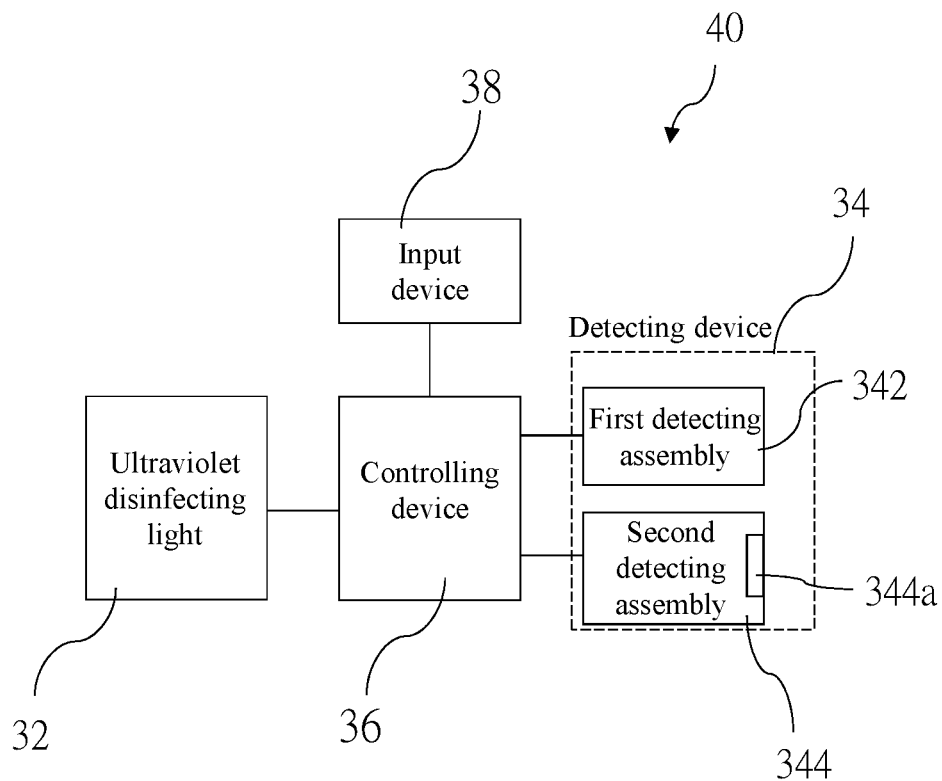
FIG. 6 is a block diagram of the disinfection system of a third embodiment according to the present invention.

A disinfection system 40 of an elevator equipment of the third embodiment according to the present invention is shown in FIG. 6, wherein the disinfection system 40 includes a structure which is similar to the disinfection system 30 of the first embodiment, except that the first detecting assembly 342 of the detecting device 34 is for detecting the temperature of the space. The first detecting assembly 342 can be a non-contact temperature sensor, such as a pyroelectric infrared radial sensor or a thermopile temperature sensor. The second detecting assembly 344, which is an image recognition and processing module as an example, is for detecting the movement state. The second detecting assembly 344 includes an imaging sensor 344a to capture images in the space 100 and recognizes the movement state accordingly. Wherein, a first state indicates that it is determined from the images that there is no moving target in the space 100 while a second state indicates that it is determined from the images that there is a moving target in the space 100. In the current embodiment, the moving target is a heat-generating or non-heat object. In one embodiment, the second detecting assembly 344 can be a motion sensor to detect a moving target, such as microwave, laser, radar, etc.

In the current embodiment, the imaging range of the second detecting assembly 344 further covers the entrance 102 and it is determined from the images whether the entrance 102 is blocked by the door 12. When the detecting device 34 detects that the entrance is blocked by the door, the controlling device 36 performs the same control steps as the first embodiment.

The controlling device 36 controls the ultraviolet disinfecting light 32 to be turned on when the detecting device 34 detects that the temperature is less than the predetermined temperature and the movement state is the first state. In other words, when the controlling device 36 determines that there is no heat-generating or non-heat moving target in the space 10 at present, the space 100 of the car 10 is going to be disinfected.

The remaining control steps of the controlling device 36 are the same as the first embodiment and need not be given here. Among the closing conditions of the current embodiment, the controlling device 36 controls the ultraviolet disinfecting light 32 to be turned off when the second detecting device 344 recognizes from the images that the door 12 does not block the entrance 102.

The disinfection system 40 of the current embodiment can be applied to the second embodiment as well.

Figure 7:
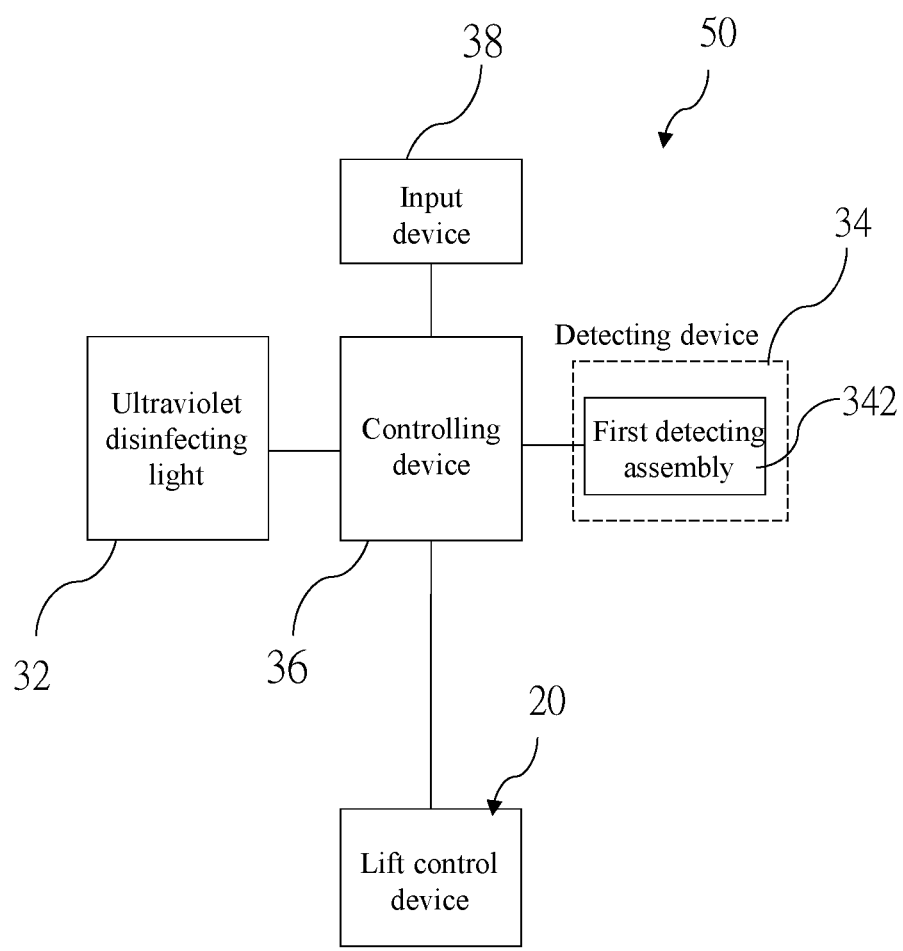
FIG. 7 is a block diagram of the disinfection system of a fourth embodiment according to the present invention.

A disinfection system 50 of the elevator equipment of a fourth embodiment according to the present invention is shown in the FIG. 7, wherein the disinfection system 50 includes a structure which is similar to the disinfection system 30 of the first embodiment, except that the detecting device 34 is not provided with a second detecting assembly. That is, whether the door 12 blocks the entrance 102 is not detected by the detecting device 34 but by the lift control device 20. In addition, the lift control device 20 can further detect the load of the car 10.

The controlling device 36 is connected to the lift control device 20 in a wired or wireless way. Before the ultraviolet disinfecting light 32 is turned on, the controlling device 36 controls the ultraviolet disinfecting light 32 not to be turned on when the lift control device 20 detects that the door 12 is open or when the load detected by the lift control device 20 is greater than a predetermined weight, wherein the predetermined weight can be set as 2 pounds.

When the ultraviolet disinfecting light 32 is controlled to be turned on, the controlling device 36 transmits a trigger signal to the lift control device 20 to control the car to move to a predetermined floor. The predetermined floor, such as between two adjacent floors or the highest floor, is to be disinfected, but it is not limited thereto.

In addition, during the period when the ultraviolet disinfecting light 32 is turned on, the controlling device 36 controls the ultraviolet disinfecting light 32 to be turned off when the load detected by the lift control device 20 is greater than the predetermined weight or when the lift control device 20 detects that the door 12 is open.

Whereby, the disinfection system 50 works with the lift control device 20. The lift control device 20 can transmit an activation signal to the controlling device 36 as well, and the controlling device 36 accordingly controls the ultraviolet disinfecting light 32 to be turned on.

The aforementioned disinfection systems of the first to third embodiments are not only applied to the cars of the elevator equipments, but to the space of other rooms or compartments, such as toilets, bathrooms, or janitorial rooms, to disinfect it.

Figure 8:
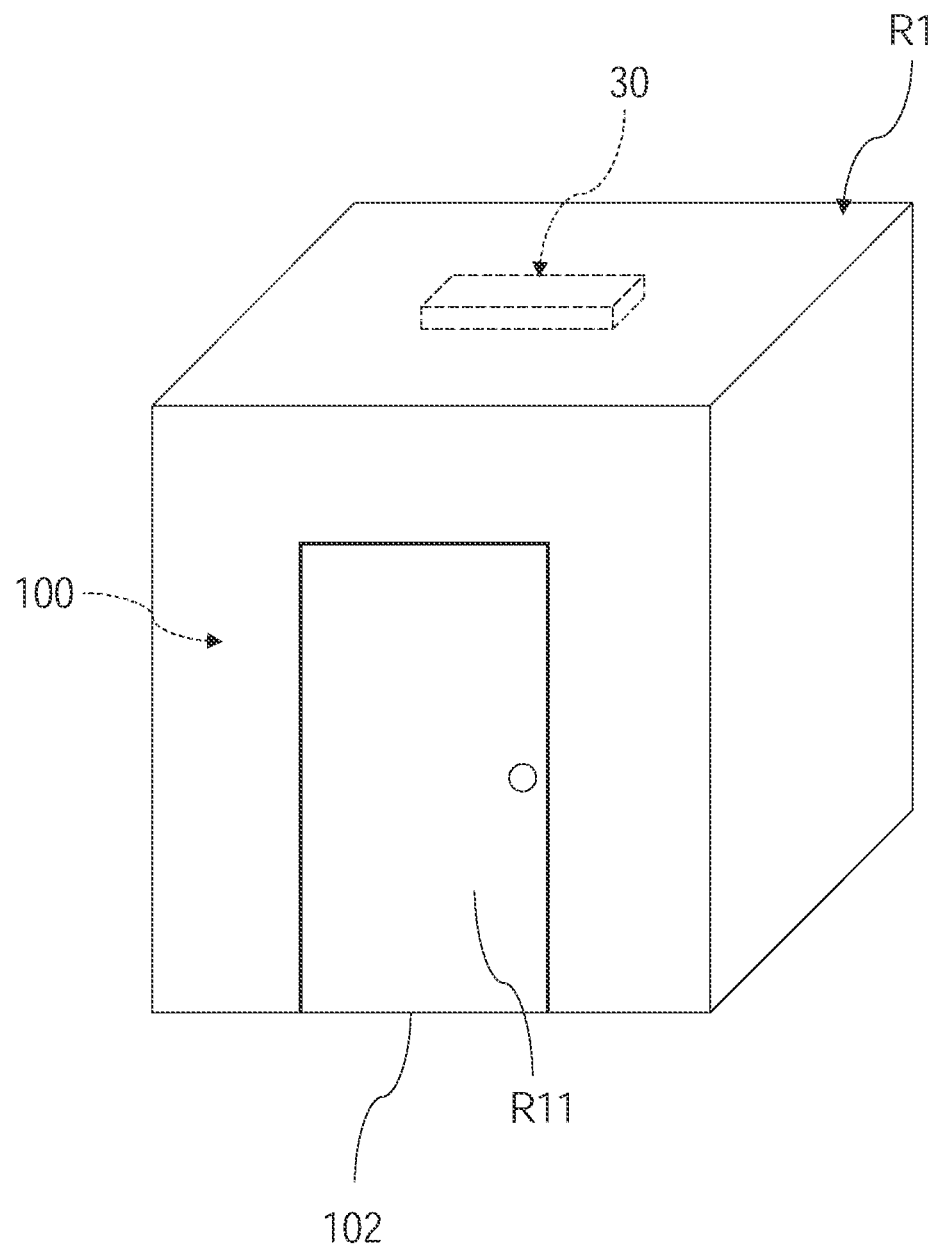
FIG. 8 is a schematic perspective view of a room to which the disinfection system is applied according to the present invention.

Take a disinfection system 1 as an example, it can be installed in the room R1 shown in FIG. 8. A door R11 is pivotally installed at the entrance to temporarily close the space 100.

Figure 9:
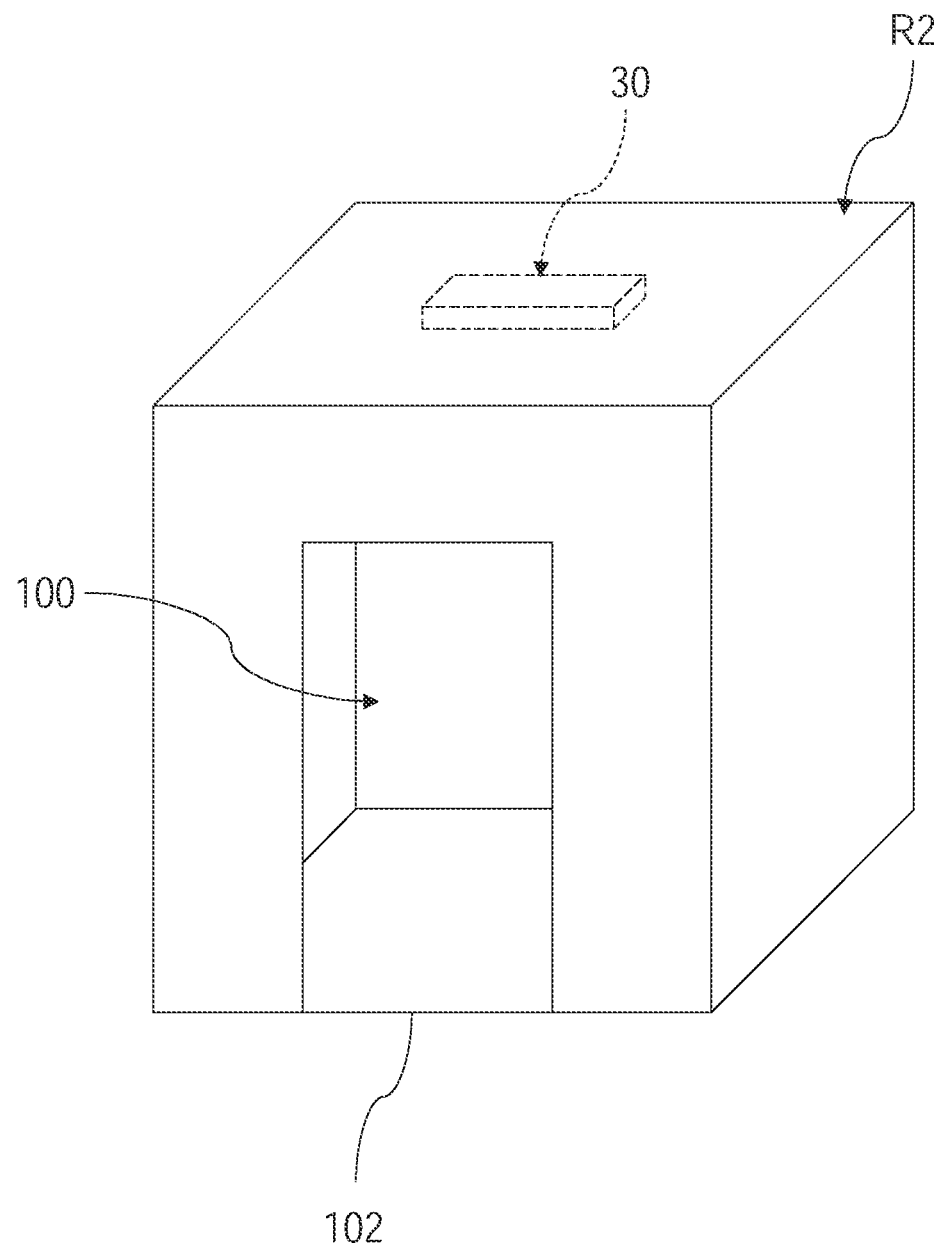
FIG. 9 is a schematic perspective view of a room to which the disinfection system is applied according to the present invention.

Take the disinfection system 1 as an example, it can also be installed in the room R2 shown in FIG. 9. The entrance 102 is not provided with a door and the detecting device 34 does not detect whether the door blocks the entrance 102 or not, either. The controlling device 36 controls the ultraviolet disinfecting light to be turned on when the detecting device 34 detects that the temperature is less than the predetermined temperature and the movement state is the first state. The closing conditions of controlling the ultraviolet disinfecting light 32 to be turned off do not include the condition that the door does not block the entrance 102.

In response to the degradation of the ultraviolet emitting components of the ultraviolet disinfecting light 32 or the deviation of the installation angle thereof, causing the insufficient disinfection effect, the present invention further provides other embodiments that reach the ultraviolet radiation dose with sufficient disinfection effect.

Figure 10:
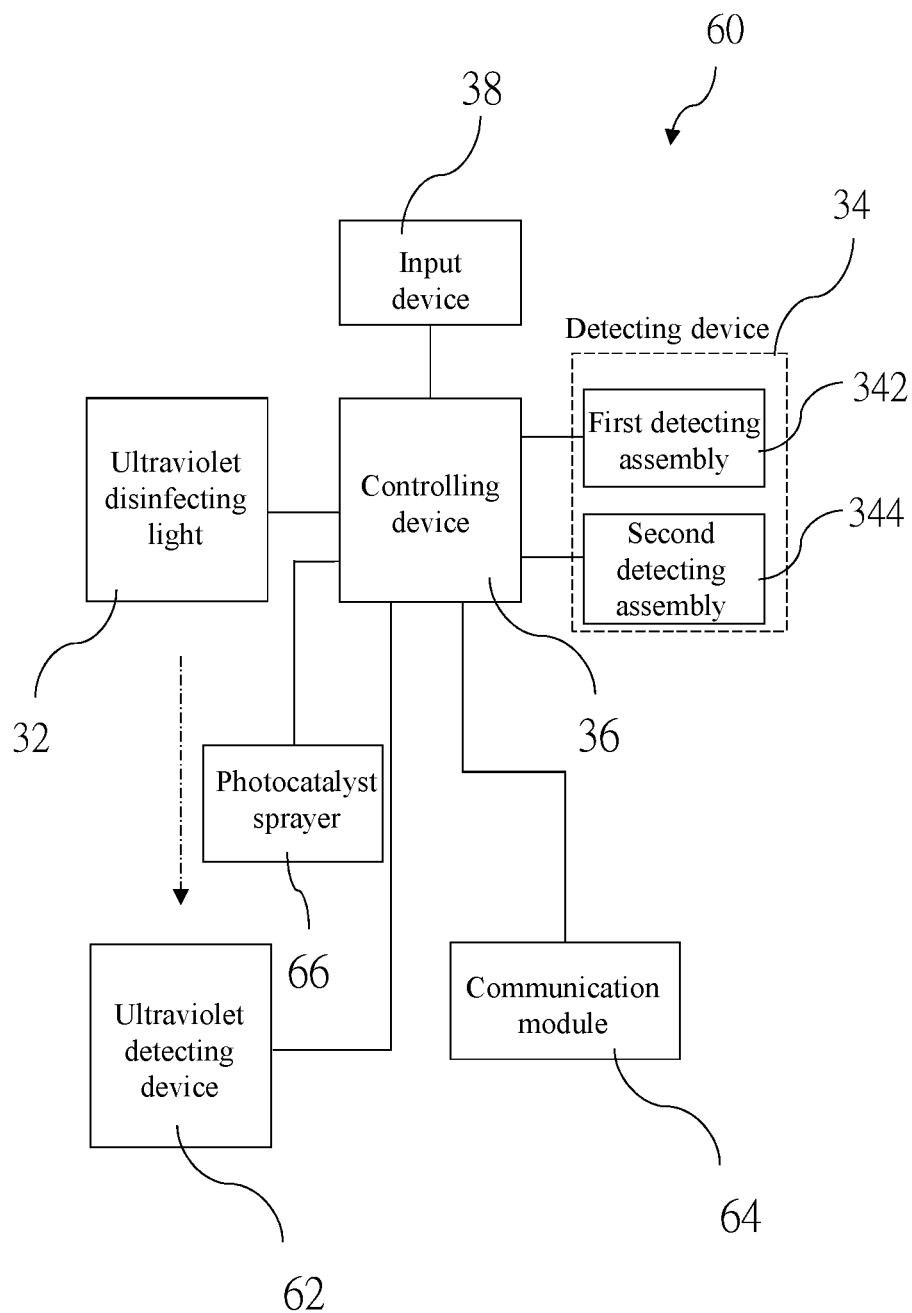
FIG. 10 is a block diagram of the disinfection system of a fifth embodiment according to the present invention.
Figure 11:
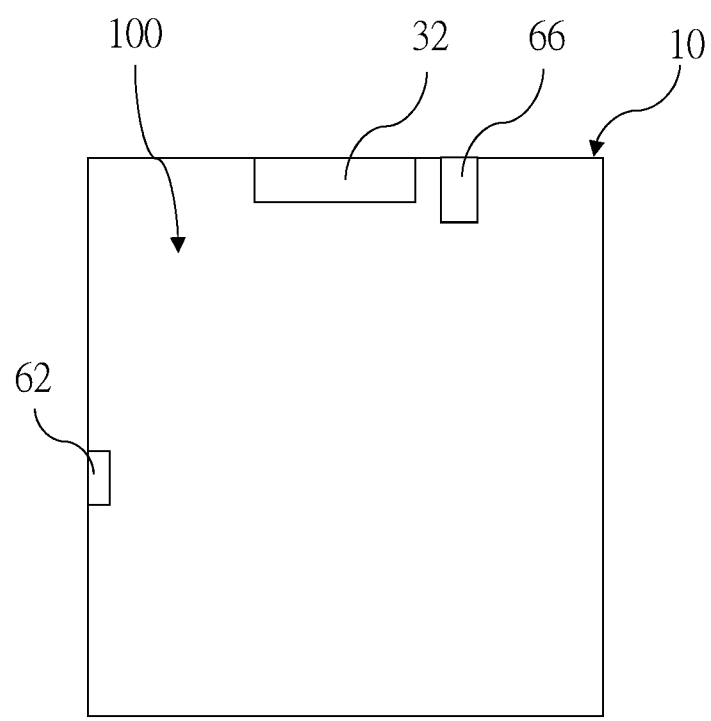
FIG. 11 is a block diagram of the disinfection system provided at the car of the fifth embodiment.

A disinfection system 60 of a fifth embodiment according to the present invention is shown in FIG. 10 and FIG. 11, wherein the disinfection system 60 is based on the structure of the first embodiment and further includes an ultraviolet detecting device 62 installed in the space 100 of the car 10 and signally connected to the controlling device 36. The ultraviolet detecting device 62 detects an intensity of the ultraviolet rays emitted by the ultraviolet disinfecting light 32. The ultraviolet detecting device 62 is signally connected to the controlling device 36 in a wired or wireless way, the difference of which is that a wireless transmission module is provided additionally in the ultraviolet detecting device 62.

When the ultraviolet disinfecting light 32 is controlled to be turned off, the controlling device 36 also controls the ultraviolet detecting device 62 not to detect ultraviolet rays so as to reduce energy consumption and extend the service life thereof.

When the ultraviolet disinfecting light 32 is controlled to be turned on, the controlling device 36 enables the ultraviolet detecting device 62 to detect the intensity of the ultraviolet rays. When the controlling device determines that the intensity of the ultraviolet rays detected by the ultraviolet detecting device 62 is less than a predetermined intensity, the controlling device controls the ultraviolet disinfecting light 32 to increase the ultraviolet radiation dose of the ultraviolet rays emitted by the ultraviolet disinfecting light 32.

In the current embodiment, when the ultraviolet disinfecting light 32 is controlled to be turned on and after an irradiation time, the controlling device 36 controls the ultraviolet disinfecting light 32 to be turned off. During the irradiation time, the controlling device 36 controls the ultraviolet disinfecting light 32 to extend the irradiation time when the intensity of the ultraviolet rays is less than the predetermined intensity so as to reach the ultraviolet radiation dose. The controlling device 36 correspondingly extends the irradiation time according to the detected intensity of the ultraviolet rays, and the extended irradiation time is inversely proportional to the intensity of the ultraviolet rays.

The controlling device 36 has a built-in corresponding relationship between different intensity of the ultraviolet rays and different irradiation times, and the corresponding relationship can be a corresponding table or a corresponding formula. The controlling device 36 obtains a corresponding irradiation time out of the corresponding relationship according to the detected intensity of the ultraviolet rays and then controls the ultraviolet disinfecting light 32 to be turned off after reaching the irradiation time, so as to get the required ultraviolet radiation dose. In other words, the lower the detected irradiation intensity, the longer the irradiation time, so that the ultraviolet radiation dose is increased to achieve a good disinfection effect to avoid insufficient disinfection effect.

The irradiation time is normally a first predetermined time when the detected intensity of the ultraviolet rays is greater than the predetermined intensity. If the detected intensity of the ultraviolet rays is less than the predetermined intensity after the ultraviolet disinfecting light 32 is controlled to be turned on, the controlling device uses a ratio of the detected intensity of the ultraviolet rays to the predetermined intensity so as to increase accordingly the irradiation time to a second predetermined time. For example, the first predetermined time is 30 minutes. If the ratio of the intensity of the ultraviolet rays to the predetermined intensity is 80%, the corresponding formula is (100+(100−80))%=120%, and the irradiation time is the first predetermined time multiplied by 120%, that is, the second predetermined time is 36 minutes and the irradiation time is extended by 6 minutes (20%).

The controlling device 36 transmits a warning message when the extended irradiation time reaches a critical time, wherein the critical time can be 1.5 to 2 times the first predetermined time, such as 45 to 60 minutes. When the irradiation time reaches the critical time, it means that the intensity of the ultraviolet rays is insufficient. The maintenance personnel will be reminded via the warning message to check the ultraviolet disinfecting light to see whether the ultraviolet emitting components have been excessively degraded or the installation angle has deviated.

The controlling device 36 is connected to a server (not shown) via a communication module 64, wherein the controlling device 36 transmits the warning message to the server and the server informs the maintenance personnel. The warning message can be transmitted through indicator lights and sound producing components.

The disinfecting system 60 further includes a photocatalyst sprayer 66 electrically connected to the controlling device 36. The photocatalyst sprayer 66 contains a photocatalyst suspension that can be catalyzed by ultraviolet rays.

The controlling device 36 controls the photocatalyst sprayer to spray a photocatalyst into the space 100 after the ultraviolet disinfecting light 32 is controlled to be turned on and the intensity of the ultraviolet rays is less than the predetermined intensity. The photocatalyst floats in the air or adheres to the walls or floor of the space 100. After the photocatalyst is catalyzed by the ultraviolet rays, it produces a disinfection effect. In this way, the disinfection effect is increased and the problem of poor disinfection effect caused by the decrease of intensity of the ultraviolet rays is solved.

As mentioned above, the irradiation time is controlled to increase the ultraviolet radiation dose. In one embodiment, the controlling device 36 controls the ultraviolet disinfecting light 32 to increase the intensity of the ultraviolet rays when the intensity of the ultraviolet rays is less than the predetermined intensity so as to reach the required ultraviolet radiation dose. The controlling device 36 can increase the current supplied to the ultraviolet emitting components, which are the ultraviolet emitting diodes as an example, to enhance the intensity of the ultraviolet rays emitted by the ultraviolet emitting diodes. If the performance of the ultraviolet emitting diodes is well, the intensity of the ultraviolet rays can be higher than the predetermined intensity again. If the intensity of the ultraviolet rays cannot reach the predetermined intensity after the increase, the irradiation time can be extended as mentioned above to reach the required ultraviolet radiation dose.

The means of detecting the intensity of the ultraviolet rays and those of controlling the ultraviolet radiation dose when the intensity of the ultraviolet rays is less than the predetermined intensity can be applied to the second embodiment.

Figure 12:
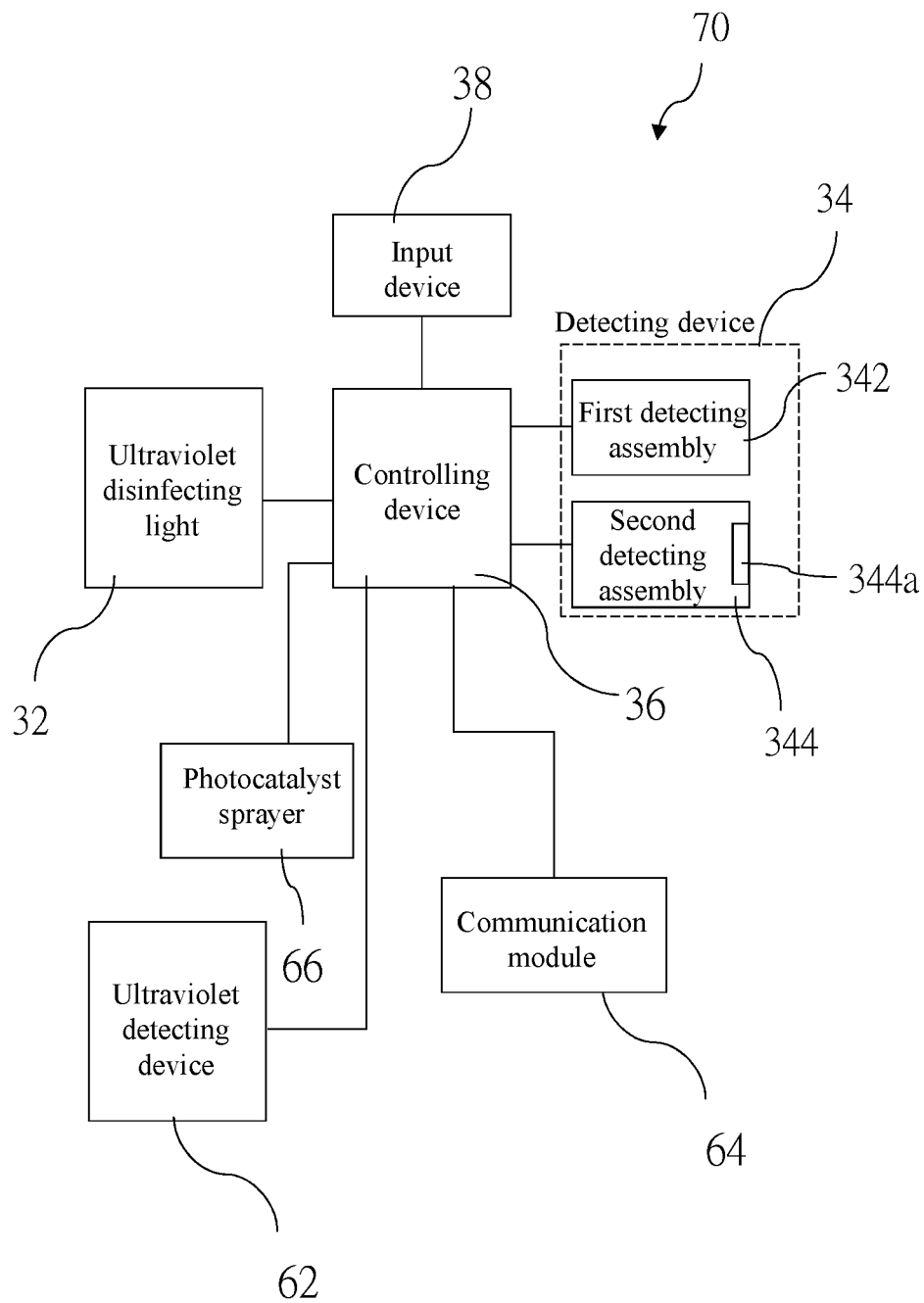
FIG. 12 is a block diagram of the disinfection system of a sixth embodiment according to the present invention.
Figure 13:
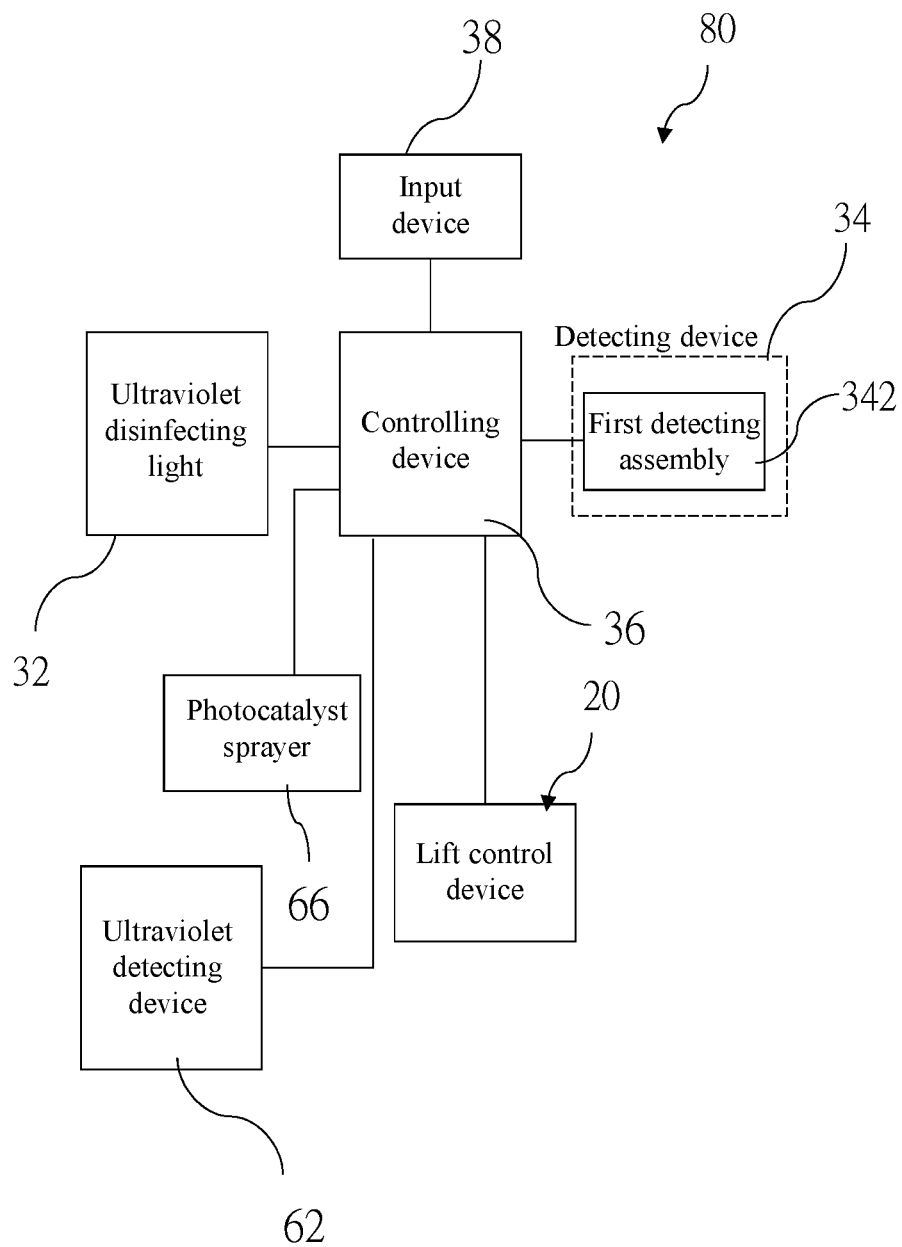
FIG. 13 is a block diagram of the disinfection system of a seventh embodiment according to the present invention.

A disinfection system 70 of a fifth embodiment according to the present invention is shown in FIG. 12, wherein the disinfection system 70 is based on the structure of the third embodiment and is further provided with the ultraviolet detecting device 62 and the photocatalyst sprayer 66. A disinfection system 80 of a sixth embodiment according to the present invention is shown in FIG. 13, wherein the disinfection system 80 is based on the structure of the fourth embodiment and is further provided with the ultraviolet detecting device 62 and the photocatalyst sprayer 66.

Both the fifth and the sixth embodiments can increase the ultraviolet radiation dose when the intensity of the ultraviolet rays is insufficient so as to avoid poor disinfection effect. In the fourth to sixth embodiments, the photocatalyst sprayer 36 can optionally not be provided.

The disinfection systems of the foregoing embodiments can also be applied to spaces on vehicles, such as automobiles, airplanes, and ships.

It must be pointed out that the embodiments described above are only some embodiments of the present invention. All equivalent structures which employ the concepts disclosed in this specification and the appended claims should fall within the scope of the present invention.

What is claimed is:

1. A disinfection system applied to a space, wherein the space has an entrance communicating with an outside thereof, comprising:
   an ultraviolet disinfecting light which can be turned on or off under control and emits ultraviolet rays to the space when it is turned on;
   a controlling device which is connected to the ultraviolet disinfecting light and controls the ultraviolet disinfecting light to be turned on or off;
   an ultraviolet detecting device which is signally connected to the controlling device and is for detecting an intensity of the ultraviolet rays emitted by the ultraviolet disinfecting light;
   a detecting device which detects a temperature and a movement state in the space, wherein the movement state is one of a first state and a second state, the first state indicates that there is no moving target in the space and the second state indicates that a moving target is in the space; the controlling device controls the ultraviolet disinfecting light to be turned on when the detecting device detects that the temperature is less than a predetermined temperature and the movement state is the first state; and
   wherein the controlling device controls the ultraviolet disinfecting light to increase an ultraviolet radiation dose of the ultraviolet rays emitted by the ultraviolet disinfecting light after the ultraviolet disinfecting light is turned on and the intensity of the ultraviolet rays is less than a predetermined intensity.

2. The disinfection system of claim 1, wherein the controlling device controls the ultraviolet disinfecting light to be turned on and after an irradiation time, the ultraviolet disinfecting light is controlled to be turned off; during the irradiation time, the controlling device controls the ultraviolet disinfecting light to increase the intensity of the ultraviolet rays emitted by the ultraviolet disinfecting light when the intensity of the ultraviolet rays is less than the predetermined intensity so as to reach the ultraviolet radiation dose.

3. The disinfection system of claim 2, wherein the controlling device further controls the ultraviolet disinfecting light to extend the irradiation time so as to reach the ultraviolet radiation dose.

4. The disinfection system of claim 1, wherein the controlling device controls the ultraviolet disinfecting light to be turned on and after an irradiation time, the ultraviolet disinfecting light is controlled to be turned off; during the irradiation time, the controlling device controls the ultraviolet disinfecting light to extend the irradiation time when the intensity of the ultraviolet rays is less than a predetermined intensity so as to reach the ultraviolet radiation dose.

5. The disinfection system of claim 4, wherein the controlling device correspondingly extends the irradiation time according to the intensity of the ultraviolet rays detected by the ultraviolet detecting device when the intensity of the ultraviolet rays is less than the predetermined intensity, and the extended irradiation time is inversely proportional to the intensity of the ultraviolet rays.

6. The disinfection system of claim 5, wherein the controlling device transmits a warning message when the extended irradiation time reaches a critical time.

7. The disinfection system of claim 1, comprising a photocatalyst sprayer electrically connected to the controlling device, wherein the controlling device controls the photocatalyst sprayer to spray a photocatalyst into the space after the ultraviolet disinfecting light is controlled to be turned on and the intensity of the ultraviolet rays is less than the predetermined intensity.

8. The disinfection system of claim 1, wherein the entrance of the space is provided with a door movably blocking the entrance; the detecting device includes an image recognition and processing module which captures images of the space and recognizes the movement state from the images; after the ultraviolet disinfecting light is controlled to be turned on, the controlling device controls the ultraviolet disinfecting light to be turned off when the image recognition and processing module recognizes out of the images that the door does not block the entrance.

9. The disinfection system of claim 1, including an input device connected to the controlling device and for inputting a time value for the controlling device to set as an irradiation time, wherein the controlling device controls the ultraviolet disinfecting light to be turned on and after the irradiation time, the ultraviolet disinfecting light is controlled to be turned off.

10. The disinfection system of claim 1, wherein the detecting device divides the space into a plurality of detection areas and detects the temperature and the movement states of each detection area; when the temperature detected at any detection area appears a predetermined temperature difference within a predetermined time, the temperature detected at any detection area is higher than the predetermined temperature, or the movement state detected at any detection area is the second state, the controlling device records the corresponding detection area as an enhanced area; the controlling device controls the ultraviolet disinfecting light to be turned on and to increase the ultraviolet radiation dose of the enhanced area when the detecting device detects the temperature of each detection area is less than the predetermined temperature and the movement state is the first state.

11. The disinfection system of claim 10, wherein the ultraviolet disinfecting light includes a plurality of ultraviolet light emitting components, each detection area respectively corresponds to at least one of the ultraviolet light emitting components; during an irradiation time, the controlling device controls the intensity of the ultraviolet rays of the at least one ultraviolet light emitting component corresponding to the enhanced area to be a first light intensity, and controls the intensity of the ultraviolet rays of the at least one ultraviolet light emitting component corresponding to the other detection area to be a second light intensity; the first light intensity is greater than the second light intensity.

12. The disinfection system of claim 11, wherein the ultraviolet disinfecting light includes a plurality of ultraviolet light emitting components, each detection area respectively corresponds to at least one of the ultraviolet light emitting components; during a first irradiation time, the controlling device controls the intensity of the ultraviolet light emitting components to be the same light intensity; after reaching the first irradiation time, the controlling device keeps the at least one ultraviolet light emitting component corresponding to the enhanced area to be turned on and controls the at least one ultraviolet light emitting component corresponding to the other detection area to be turned off; after reaching a second irradiation time, the controlling device controls at least one of the ultraviolet light emitting component corresponding to the enhanced area to be turned off.

13. A disinfection system applied to a space, wherein the space has an entrance communicating with an outside thereof, comprising:
an ultraviolet disinfecting light which can be turned on or off under control and emits ultraviolet rays to the space when it is turned on;
a controlling device which is connected to the ultraviolet disinfecting light and controls the ultraviolet disinfecting light to be turned on or off;
an ultraviolet detecting device which is signally connected to the controlling device and is for detecting an intensity of the ultraviolet rays emitted by the ultraviolet disinfecting light;
wherein the controlling device controls the ultraviolet disinfecting light to increase an ultraviolet radiation dose of the ultraviolet rays emitted by the ultraviolet disinfecting light after the ultraviolet disinfecting light is turned on and the intensity of the ultraviolet rays is less than a predetermined intensity; and
wherein the entrance of the space is provided with a door movably blocking the entrance; the detecting device includes an image recognition and processing module which captures images of the space; after the ultraviolet disinfecting light is controlled to be turned on, the controlling device controls the ultraviolet disinfecting light to be turned off if the image recognition and processing module recognizes out of the images that the door does not block the entrance.

14. An elevator equipment, comprising:
a car;
a lift control device for controlling the lift of the car; and
the disinfection system of claim 1 installed at the car, the space located inside the car.

15. The elevator equipment of claim 14, wherein the controlling device is connected to the lift control device; when the ultraviolet disinfecting light is controlled to be turned on, the controlling device accordingly transmits a trigger signal to the lift control device to control the car to move to a predetermined floor.

16. The elevator equipment of claim 14, wherein the controlling device is connected to the lift control device; the lift control device transmits an activation signal to the controlling device, and the controlling device accordingly controls the ultraviolet disinfecting light to be turned on.

17. The elevator equipment of claim 14, wherein the controlling device is connected to the lift control device; the lift control device detects a load of the car; the controlling device controls the ultraviolet disinfecting light to be turned off when the load detected by the lift control device is greater than a predetermined weight.

18. The elevator equipment of claim 14, wherein the car has a door; the controlling device is connected to the lift control device; the lift control device detects whether the car is open or not; the controlling device controls the ultraviolet disinfecting light to be turned off when the door is detected as open.

* * * * *